United States Patent [19]

Leary

[11] Patent Number: 4,951,691
[45] Date of Patent: Aug. 28, 1990

[54] METHOD OF TREATING AND CURING SMOKING HABITS AND THE LIKE IN ADULTS

[76] Inventor: Robyn Leary, 4101 Cathedral Ave., NW., Apt. 1109, Washington, D.C. 20016

[21] Appl. No.: 602,537

[22] Filed: Apr. 20, 1984

Related U.S. Application Data

[63] Continuation of Ser. No. 383,551, Jun. 1, 1982, abandoned.

[51] Int. Cl.⁵ .................... A24F 47/00; G09B 14/00
[52] U.S. Cl. .................................. 131/270; 434/236
[58] Field of Search ..................... 131/270; 434/236

Primary Examiner—V. Millin
Attorney, Agent, or Firm—C. Emmett Pugh

[57] ABSTRACT

A method for treating and curing the smoking habit and the like in adults, including the use of an oral, oval, disc-shaped object, which is of the size that can be easily placed in the mouth and on the tongue of the user. When the urge to smoke arises, the oral object is placed in the mouth on the tongue, and the object is sucked and moved about the mouth under the action of the tongue, causing salivation, gastric acid secretion, and stimulation of the cranial nerve endings in the tongue in a like-fashion to the stimulation caused by smoking cigarettes and the like. The invention can also be used to treat and cure over-eating. The oral device is preferably attached to a necklace-like chain or the like for wearing by the user about the neck, making the oral device readily available for oral use.

3 Claims, 1 Drawing Sheet

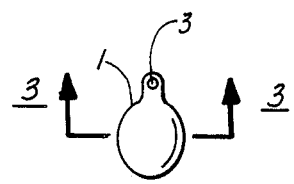
FIG. 1
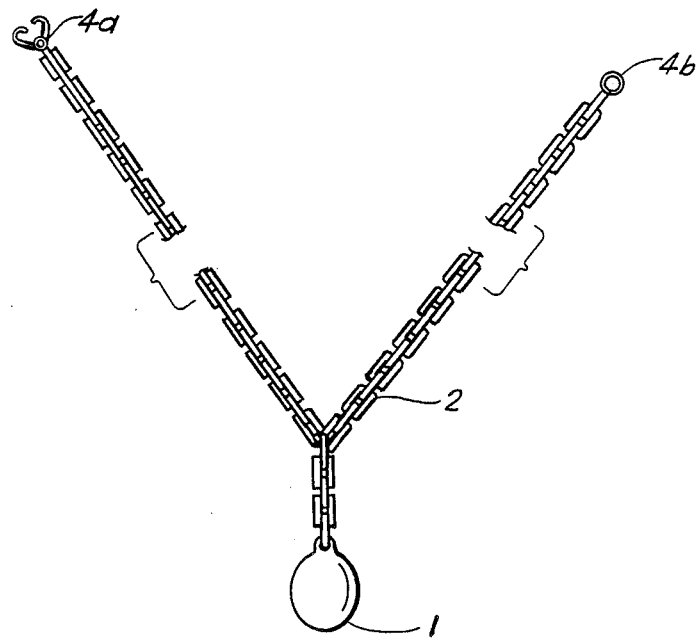
FIG. 2
FIG. 3
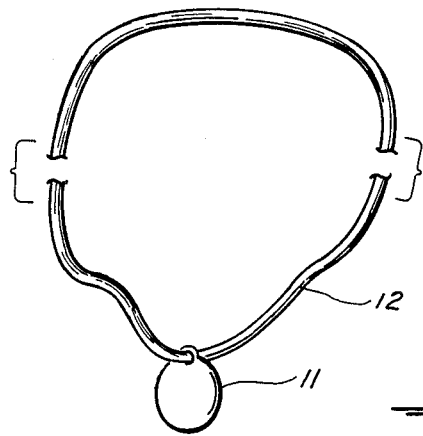
FIG. 4

METHOD OF TREATING AND CURING SMOKING HABITS AND THE LIKE IN ADULTS

This application is a continuation of application Ser. No. 06/383,551, filed 6/1/82 now abandoned.

BACKGROUND OF THE INVENTION

1. Field of Invention

The present invention relates to the method of treating and curing the smoking habits and other related maladies prevalent among adults, and to provide an oral device particularly useful in such a method.

2. Prior Art and General Background

Smoking is a complex activity which starts with mechanical and physical steps. When these steps are performed in a habitual or ritualistic fashion, the end result or goal is the satisfaction of physical and Psychological needs.

The mechanical steps involved in smoking include: carrying cigarettes, lighting them, placing them between the lips, sucking on them, inhaling the smoke, exhaling, holding the lighted cigarette, and repeating the maneuver. A physical need that is satisfied by these steps is the achievement of a blood level of nicotine and other substances. This is somewhat that habituated smoker's body comes to sense a worthwhile goal. Psychological needs that are satisfied by the steps involved in smoking are very basic and infantile, including ingesting, sucking, grasping, and repetitive hand to mouth activity.

That the psychological needs of smoking are of as great importance as the chemical ones is amply illustrated by consistent observations on persons who have recently tried to quit. They eat more and gain weight, "don't know what to do" with their hands, and experience extreme psychological discomfort—manifested as irritability. While the loss of chemical satisfaction contributes to this by unknown and indirect mechanisms, the substitution of food for smoking substitutes the importance of the sucking and ingestion behavior.

This habitual, complex activity can be stopped at any point. One approach, supplying one of the goals by administering nicotine by various other routes, has been largely unsuccessful—and has its own chemical hazards.

It is believed in the present invention that an oral device to modify the physical activities has the best chance of success in individuals who wish to break the smoking habit.

Oral devices for pacifying babies, particularly during the teething process, a non-analogous art, are of course well known. Typical examples of such pacifiers are shown in the below listed patents:

| Patentee(s) | Patent No. | Issue Date |
| --- | --- | --- |
| Grabler | 462,763 | Nov. 10, 1891 |
| Palmer | 1,623,969 | April 12, 1927 |
| Johnson | 2,595,462 | May 6, 1952 |
| Newmark | Des. 171,165 | Dec. 22, 1953 |
| Carden | 2,827,055 | March 18, 1958 |

It is noted that the Palmer "Teething Device for Infants" utilizes a ribbon attached to the oral device for suspending the device about the neck as a pendant. The baby teething device of the Johnson patent likewise includes a chain for attaching the device to the wrist of the baby.

Also, oral devices serving as orthodontic mouth exercisers for juveniles in the age group from about three to fourteen years, another non-analogous art, are also known. See for example the Pat. No. 3,187,746 issued to Warren E. Gerber on June 8, 1965.

The foregoing prior teachings are, it is believed, not relevant to the treatment and cure of smoking habits and the like in adults.

3. Summary Discussion of the Invention:

The present invention provides an oral device and technique for treating and curing the smoking habit and the like in adults. The oral device is carried in a reassuring way, like a cigarette pack, but closer to the mouth. It is handy for hand-to-mouth activity. The needs to ingest and suck are satisfied—the shape and texture are designed to be particularly satisfying in this regard.

An important physical modification produced by the present invention is its substitution for cigarettes in the complex activity of smoking. The end result of its use is the most important physical sodification of all: the cessation of tobacco use with deposition in the lungs and bloodstream of carcinogens and other injurious substances such as carbon monoxide, with their devastating results on health.

The use of the oral device of the present invention also causes salivation, gastric acid secretion, and stimulation of the cranial nerve endings in the tongue, in like fashion to the stimulation caused by smoking cigarettes and the like. Other physical effects also occur in the body as a result of the use of the present invention, including perhaps the production of endorphins in the bloodstream.

It is believed that it is the similarity (same nerve pathways) of the stimulation caused by cigarette smoking (without invoking any of the chemical affects of nicotine) that is important to help break the habitual craving for such stimulation by cigarettes.

In use, the oral device of the present invention is put in the adult mouth on the tongue when the urge to smoke arises. The relatively small object is moved about the mouth under the action of the tongue.

In addition to treating the smoking habit, the present invention can, in like fashion, be used to treat over-eating wherein the same oral device is inserted in the mouth whenever an unnecessary urge to eat arises. As used herein, the phrases "smoking habit", "desire to smoke", "urge to smoke" are considered equivalent to and inclusive of an over-eating habit, a desire to est, and an urge to eat, respectively. In like fashion the present invention can be used to treat a drug habit, and such use is likewise considered included in the phrases "smoking habit and the like," etc. Also, the work "adult" as used herein is meant to include those above the age of juveniles, for example from about the age of sixteen on up.

BRIEF DESCRIPTION OF DRAWINGS

For a further understanding of the nature and objects of the present invention, reference should be had to the following detailed description, taken in conjunction with the accompanying drawings, in which like parts are given like reference numerals and wherein:

FIG. 1 is partial, overall view of the oral device and associated necklace used in the preferred embodiment of the method of the present invention; while FIG. 2 is side-close-up view of the oral device of FIG. 1; and FIG. 3 is a top-cross-sectional view of the oral device of FIG. 1, taken along the section lines 3—3 of FIG. 2.

FIG. 4 is a view similar to FIG. 1, but of a second embodiment of the oral device for use in the method of the present invention.

DETAILED DESCRIPTION OF THE PREFERRED EMBODIMENTS

The preferred embodiment of the oral device used in the preferred method of the present invention is illustrated in FIGS. 1-3.

The oral device 1 comprises an oval, disc-shape having a size which can be easily placed into the mouth and on the tongue of the adult user, having dimensions of for example two by two-and-a-half by one-half centimeters. The oral device 1 is preferably attached to a neck-encircling member 2, which can be for example a necklace-like chain having claps 4a, 4b made of for example plastic or stainless steel and is connected to the device 1 by means of the opening 3. A further exemplary embodiment is illustrated in FIG. 4 and includes an oral device 11 of an FDA approved acrylic material suspended on a nylon lanyard 12 designed to be worn around the neck.

The oral device 1 is non-edible and is preferably made of a hard plastic that can be for example a simple, completely polymerized polymer, being chemically inert and one hundred percent safe. The device 1 is preferably slightly textured to create friction and prevent the inadvertent sliding of the device 1 into the throat during use.

In use, when the urge to smoke arises in the adult, the oral device 1 is placed in the user's mouth and preferably on the tongue. The oral device 1 is then sucked by the user and moved about the mouth of the user under the section of the tongue. This causes salivation, gastric acid secretion and stimulation of the cranial nerve endings in the tongue, in like fashion to the stimulation caused by smoking cigarettes and the like.

The oral device 1 is thus preferably worn as a necklace, with the oral device 1 placed in the mouth when needed to respond to and satisfy the smoking urge. The oral device 1, held in the mouth, satisfies the oral craving, which is the impulse that drives the type of compulsive behavior involved in a smoking habit and the like.

The use of the a neck-encircling member 2, for example in the form of a necklace, not only allows for the handy location of the oral device 1, but it also protects the user from accidental swallowing or inhaling the device.

After testing, the disc-like shape of the oral device 1 has been found to be the most preferable as an orally-satisfying shape. However, of course, other physical shapes and sizes are possible within the method of the present invention.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1., A method for treating an adult person's desire to smoke cigarettes and the like, comprising the following steps:

(a) providing to an adult a small, non edible solid, hard, disc shaped object of a size having a textured surface for creating traction to be put in the adult mouth and to fit on the tongue;

(b) when the urge to smoke and the like arises, placing the small object in the mouth;

(c) sucking the small object and moving it about the mouth under the action of the tongue, causing salivation, gastric acid secretion, and stimulation of the cranial nerve endings in the tongue, in like fashion to the stimulation caused by smoking and the like, the textured surface of the small object causing traction and preventing the inadvertent sliding of the small object into the throat during use; and (d) repeating steps "b" and "c" using the same small object until the desire to smoke cigarettes is reduced.

2. The method of claim 1, wherein in step "a" there is included the step of providing the small object with a flexible, neck-encircling member for suspending the object in front of the user about the users neck, and in step "c" there is included the additional step of further preventing the object from being accidentally swallowed by suspending the object about the neck by the flexible, neck-encircling member.

3. A method for treating an adult person's desire to smoke cigarettes and the like, comprising the following steps:

(a) providing to an adult a small, non edible solid, hard, disc shaped object of a size to be put in the adult mouth and to fit on the tongue and providing the small object with a flexible, neck encircling member for suspending the object in front of the user about the user's neck;

(b) when the urge to smoke and the like arises, placing the small object in the mouth;

(c) sucking the small object and moving it about the mouth under the action of the tongue, causing salivation, gastric acid secretion, and stimulation of the cranial nerve endings in the tongue, in like fashion to the stimulation caused by smoking cigarettes and the like, preventing the object from being accidentally swallowed by suspending the object about the neck by the flexible, neck-encircling member; and (d) repeating steps "b" and "c" using the same small object until the desire to smoke cigarettes is reduced.

* * * * *